United States Patent
Brooks (10) Patent No.: US 10,350,438 B2
(45) Date of Patent: Jul. 16, 2019

(54) SYSTEM AND METHOD FOR TARGET TRACKING USING A QUALITY INDICATOR DURING RADIATION THERAPY

(71) Applicant: ELEKTA Ltd., Montreal (CA)

(72) Inventor: Rupert Brooks, Montreal (CA)

(73) Assignee: Elekta LTD., Montreal (CA)

( * ) Notice: Subject to any disclaimer, the term of this patent is extended or adjusted under 35 U.S.C. 154(b) by 18 days.

(21) Appl. No.: 15/740,945

(22) PCT Filed: Jun. 29, 2016

(86) PCT No.: PCT/IB2016/001029
§ 371 (c)(1),
(2) Date: Dec. 29, 2017

(87) PCT Pub. No.: WO2017/001920
PCT Pub. Date: Jan. 5, 2017

(65) Prior Publication Data
US 2018/0193674 A1    Jul. 12, 2018

Related U.S. Application Data (60) Provisional application No. 62/186,743, filed on Jun. 30, 2015.

(51) Int. Cl.
*A61N 5/00*     (2006.01)
*A61N 5/10*     (2006.01)
(Continued)

(52) U.S. Cl.
CPC ......... *A61N 5/1084* (2013.01); *A61N 5/1049* (2013.01); *G06N 20/00* (2019.01);
(Continued)

(58) Field of Classification Search
CPC .... A61N 2005/1061; A61N 2005/1049; A61N 2005/1084; G06T 2207/20081; G06T 2207/30004; G06N 20/00
See application file for complete search history.

(56) References Cited

U.S. PATENT DOCUMENTS 8,548,561 B2 * 10/2013 Vortman ............... A61B 5/416
600/407
2007/0081712 A1   4/2007 Huang et al.
(Continued)

FOREIGN PATENT DOCUMENTS

AU   2016286520 A1   1/2018
AU   2016286520 B2   9/2018
(Continued)

OTHER PUBLICATIONS

"Japanese Application Serial No. 2017-568429,Office Action dated Dec. 18, 2018", W/ English Translation, 12 pgs.
(Continued)

*Primary Examiner* — Dani Fox
(74) *Attorney, Agent, or Firm* — Schwegman LUndberg & Woessner, P.A.; Sanjay Agrawal (57) ABSTRACT

Systems and methods are provided for target tracking using a quality indicator during radiation therapy treatment. An exemplary method may include determining a localization result indicating a location of a target in a plurality of images representative of images acquired in a radiation therapy treatment session. The method may also include determining a quality indicator for each localization result. The method may further include extracting one or more features from each localization result. In addition, the method may include training the classifier using the localization result and one or more of the extracted features.

20 Claims, 6 Drawing Sheets

(51) Int. Cl.
*G06N 20/00* (2019.01)
*G16H 40/60* (2018.01)

(52) U.S. Cl.
CPC ..... *G16H 40/60* (2018.01); *A61N 2005/1061* (2013.01); *G06T 2207/20081* (2013.01); *G06T 2207/30004* (2013.01)

(56) References Cited

U.S. PATENT DOCUMENTS

| | | |
|---|---|---|
| 2009/0297007 A1 | 12/2009 | Cosatto et al. |
| 2013/0030283 A1 | 1/2013 | Vortman |
| 2014/0170483 A1 | 6/2014 | Zhang et al. |
| 2015/0169836 A1 | 6/2015 | Vahala et al. |

FOREIGN PATENT DOCUMENTS

| | | |
|---|---|---|
| CN | 101540048 | 9/2009 |
| EP | 3316965 A1 | 5/2018 |
| JP | 2008520318 A | 6/2008 |
| JP | 2008528102 A | 7/2008 |
| JP | 2012187139 A | 10/2012 |
| JP | 2014212820 A | 11/2014 |
| RU | 2427911 | 8/2011 |
| WO | WO-2005001742 A2 | 1/2005 |

OTHER PUBLICATIONS

"Australian Application Serial No. 2016286520, Response filed Aug. 25, 2018 to First Examination Report dated May 24, 2018", 18 pgs.

"European Application Serial No. 16817314,4, Extended European Search Report dated Dec. 7, 2018", 7 pgs.

Written Opinion of the International Searching Authority, dated Oct. 28, 2016, on PCT/IB2016/001029 (3 pp.).

International Search Report, dated Oct. 28, 2016, on PCT/IB2016/001029 (2 pp.).

"Australian Application Serial No. 2016286520, First Examination Report dated May 24, 2018", 3 pgs.

"Japanese Application Serial No. 2017-568429, Office Action dated Dec. 18, 2018", w English Claims, 12 pgs.

"Russian Application Serial No. 2018103211, Office Action dated Mar. 27, 2019", W English Translation, 15 pgs.

* cited by examiner

SYSTEM AND METHOD FOR TARGET TRACKING USING A QUALITY INDICATOR DURING RADIATION THERAPY

CROSS-REFERENCE TO RELATED APPLICATION

The present application is a national stage application under § 371 of International Application No. PCT/IB2016/001029, filed Jun. 29, 2016, which claims the benefit of priority to U.S. Provisional Application No. 62/186,743, filed Jun. 30, 2015, the entire contents of the above-identified applications are incorporated herein by reference.

TECHNICAL FIELD

The disclosure generally relates to radiation therapy or radiotherapy. More specifically, this disclosure relates to systems and methods for determining tracking of a target organ during radiation therapy.

BACKGROUND

Radiotherapy is used to treat cancers and other ailments in mammalian (e.g., human and animal) tissue. One such radiotherapy technique is a Gamma Knife, by which a patient is irradiated by a large number of low-intensity gamma rays that converge with high intensity and high precision at a target (e.g., a tumor). In another embodiment, radiotherapy is provided using a linear accelerator, whereby a tumor is irradiated by high-energy particles (e.g., electrons, protons, photons, ions, and the like). The placement and dose of the radiation beam must be accurately controlled to ensure the tumor receives the prescribed radiation, and the placement of the beam should be such as to minimize damage to the surrounding healthy tissue, often called the organ(s) at risk (OARS). Furthermore, in yet another embodiment, radiotherapy can be provided by brachytherapy, which allows high doses of radiation to be placed internally at specific areas of the body.

When using an external radiation therapy, the radiation beam may be shaped to match a shape of the tumor, such as by using a multileaf collimator (e.g., multileaf collimator includes multiple tungsten leaves that may move independently of one another to create customized radiation beam shapes). (Radiation is termed "prescribed" because a physician orders a predefined amount of radiation to the tumor and surrounding organs similar to a prescription for medicine).

Traditionally, for each patient, a radiation therapy treatment plan ("treatment plan") may be created using an optimization technique based on clinical and dosimetric objectives and constraints (e.g., the maximum, minimum, and mean doses of radiation to the tumor and critical organs). The treatment planning procedure may include using a three-dimensional image of the patient to identify a target region (e.g., the tumor) and to identify critical organs near the tumor. Each structure (e.g., a target, a tumor, an OAR, etc.) can be discretized into a finite number of volume cubes, known as voxels. Creation of a treatment plan can be a time consuming process where a planner tries to comply with various treatment objectives or constraints (e.g., dose volume histogram (DVH) objectives), taking into account their individual importance (e.g., weighting) in order to produce a treatment plan which is clinically acceptable. This task can be a time-consuming trial-and-error process that is complicated by the various organs at risk (OARs), because as the number of OARs increases (e.g., up to thirteen or more for a head-and-neck treatment), so does the complexity of the process. OARs distant from a tumor may be easily spared from radiation, while OARs close to or overlapping a target tumor may be difficult to spare.

Computed Tomography (CT) imaging traditionally serves as the primary source of image data for treatment planning for radiation therapy. CT images offer accurate representation of patient geometry, and CT values can be directly converted to electron densities (e.g., Hounsfield units) for radiation dose calculation. However, using CT causes the patient to be exposed to additional radiation dosage. In addition to CT images, magnetic resonance imaging (MRI) scans can be used in radiation therapy due to their superior soft-tissue contrast, as compared to CT images. MRI is free of ionizing radiation and can be used to capture functional information of the human body, such as tissue metabolism and functionality.

Imaging systems such as computed tomography (CT), ultrasound, fluoroscopy, and magnetic resonance imaging (MRI) may be used to determine the location of a target and to track the target (e.g., an organ, a tumor, and the like). MRI can be used because it provides excellent soft tissue contrast without using ionizing radiation as used by CT. An example of a radiotherapy treatment system integrated with an imaging system may include an MRI-Linac, which may use three-dimensional (3D) images of a target (e.g., a tumor). The MRI apparatus of the MRI-Linac may provide a plurality of images that corresponds to a partial map of hydrogen nuclei in tissues of the patient. The patient images may be acquired in a one-dimensional (1D) line, a two-dimensional (2D) plane, or in a 3D volume. Because organs and tumors move within a patient's body, fast and accurate 3D localization of the target is important. For instance, a target organ or tumor may move because of various types of motion (e.g., respiratory, cardiac, peristalsis or other types of patient motion).

Treatment outcomes depend upon many factors. Those factors include accurate target contouring, correct dose calculation and delivery, precise radiation beam collimation, and accurate patient positioning, which includes precise localization of a moving tumor. Typically both patient setup and intrafraction monitoring for radiation therapy treatment uses image localization using bony landmarks, fiducial markers, or soft tissue.

Images of the patient's anatomy taken at different times may be analyzed to determine the movement of this anatomy over the intervening period. This may be done between images of the same modality, or between images of different modalities. A human operator monitoring the patient's position has problems of inattention, and is not able to provide correction in real time. Therefore it is useful to apply image analysis methods to localize the anatomy, and adjust the treatment (e.g. linac gating, or MLC movement), in real time. However, most localization algorithms do not provide information whether the results of localization are adequate for determining target motion. Therefore, what is needed is a method and system that can quickly, efficiently, and automatically determine in real-time the quality of the localization of a target in an image, which can provide information as to whether the treatment decision (to adjust or not) can be considered reliable.

SUMMARY

In one aspect, the present disclosure involves a method for training a classifier for determining a quality of target localization from a plurality of images acquired by an imaging device during radiation therapy treatment to a patient. The method may include determining a localization result indicating a location of a target in a plurality of images representative of images acquired in a radiation therapy treatment session. The method may also include determining a quality indicator for each localization result. The method may further include extracting one or more features from each localization result. In addition, the method may include training the classifier using the localization result and one or more of the extracted features.

In another aspect, the present disclosure involves a method for determining a quality of target localization from a plurality of images acquired by an imaging device during radiation therapy treatment to a patient. The method may include determining a localization result indicating a location of a target in a plurality of images acquired during radiation therapy treatment to the patient. The method may also include determining a localization quality of the localization result for tracking the location of the target using a classifier. The method may further include providing to a user an indication of the localization quality or taking treatment related action based on the localization quality.

In a further aspect, the present disclosure involves a system for training a classifier for determining a quality of target localization from a plurality of images acquired by an imaging device during radiation therapy treatment to a patient. The system may include a memory for storing computer-executable instructions. The system may also include a processor communicatively coupled to the memory. The computer-executable instructions, when executed by the processor, may cause the processor to perform various operations. The operations may include determining a localization result indicating a location of a target in a plurality of images representative of images acquired in a radiation therapy treatment session. The operations may also include determining a quality indicator for each localization result. The operations may further include extracting one or more features from each localization result. In addition, the operations may include training the classifier using the localization result and one or more of the extracted features.

In another aspect, the present disclosure involves a system for determining a quality of target localization from a plurality of images acquired by an imaging device during radiation therapy treatment to a patient. The system may include a memory for storing computer-executable instructions. The system may also include a processor communicatively coupled to the memory. The computer-executable instructions, when executed by the processor, may cause the processor to perform various operations. The operations may include determining a localization result indicating a location of a target in a plurality of images acquired during radiation therapy treatment to the patient. The operations may also include determining a localization quality of the localization result for tracking the location of the target using a classifier. The operations may further include providing to a user an indication of the localization quality or taking treatment related action based on the localization quality.

In a further aspect, the present disclosure involves a non-transitory computer-readable medium that stores a set of instructions that is executable by at least one processor of a device to cause the device to perform a method for training a classifier for determining a quality of target localization from a plurality of images acquired by an imaging device during radiation therapy treatment to a patient. The method may include determining a localization result indicating a location of a target in a plurality of images representative of images acquired in a radiation therapy treatment session. The method may also include determining a quality indicator for each localization result. The method may further include extracting one or more features from each localization result. In addition, the method may include training the classifier using the localization result and one or more of the extracted features.

In a further aspect, the present disclosure involves a non-transitory computer-readable medium that stores a set of instructions that is executable by at least one processor of a device to cause the device to perform a method for determining a quality of target localization from a plurality of images acquired by an imaging device during radiation therapy treatment to a patient. The method may include determining a localization result indicating a location of a target in a plurality of images acquired during radiation therapy treatment to the patient. The method may also include determining a localization quality of the localization result for tracking the location of the target using a classifier. The method may further include providing to a user an indication of the localization quality or taking treatment related action based on the localization quality.

Additional objects and advantages of the present disclosure will be set forth in part in the following detailed description, and in part will be obvious from the description, or may be learned by practice of the present disclosure. The objects and advantages of the present disclosure will be realized and attained by means of the elements and combinations particularly pointed out in the appended claims.

It is to be understood that the foregoing general description and the following detailed description are exemplary and explanatory only, and are not restrictive of the invention, as claimed.

BRIEF DESCRIPTION OF THE DRAWINGS

In the drawings, which are not necessarily drawn to scale, like numerals may describe similar components in different views. Like numerals having letter suffixes or different letter suffixes may represent different instances of similar components. The drawings illustrate generally, by way of example, but not by way of limitation, various embodiments, and together with the description and claims, serve to explain the disclosed embodiments. When appropriate, the same reference numbers are used throughout the drawings to refer to the same or like parts. Such embodiments are demonstrative and not intended to be exhaustive or exclusive embodiments of the present apparatuses, systems, or methods.

DETAILED DESCRIPTION

Figure 1:
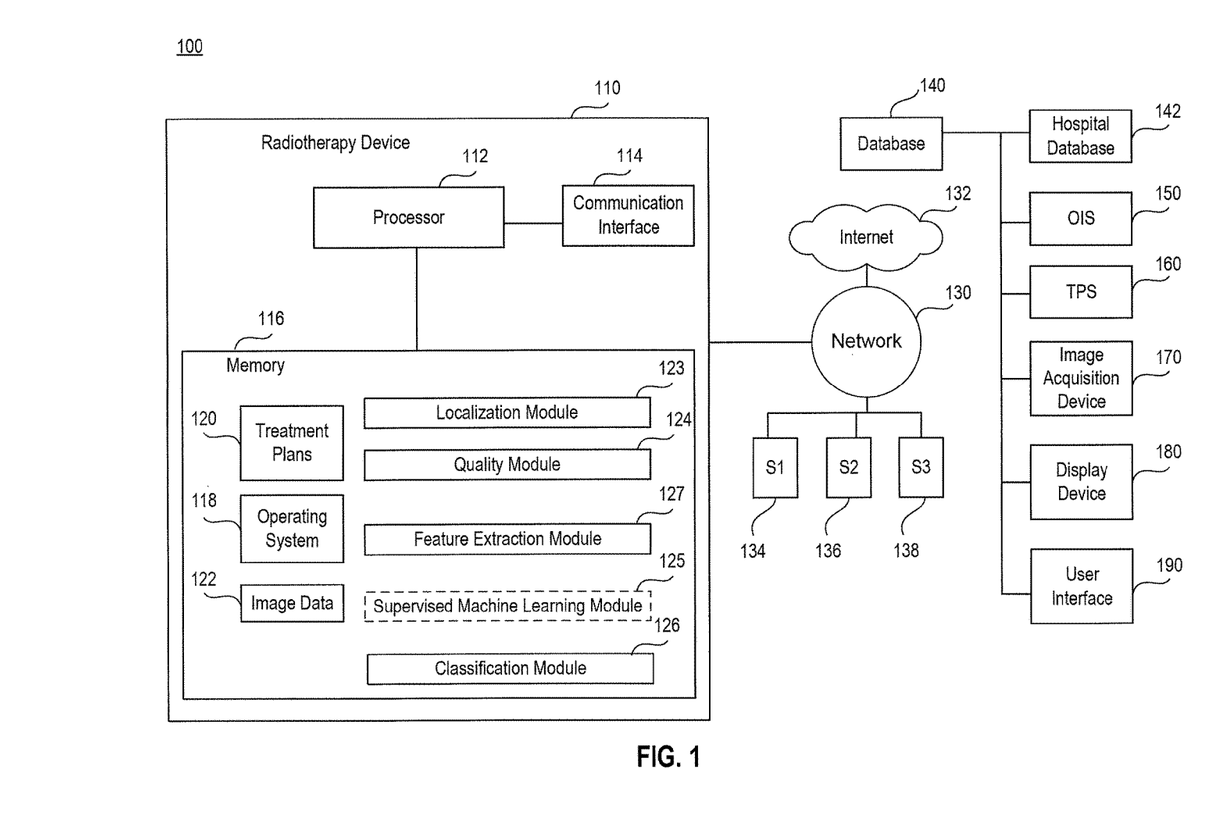
FIG. 1 illustrates an exemplary radiotherapy system to localize and track a three-dimensional target for radiation therapy.

FIG. 1 illustrates an exemplary radiotherapy system 100 for generating a radiation therapy treatment plan or updating an existing radiation therapy treatment plan using a dose distribution as a treatment objective, wherein the updated treatment plan can be used to treat a patient with radiation therapy. The radiotherapy system 100 may include a radiation therapy device 110 connected to a network 130 that is connected to the Internet 132. The network 130 can connect the radiation therapy device 110 with a database 140, a hospital database 142, an oncology information system (OIS) 150 (e.g., which may provide patient information), a treatment planning system (TPS) 160 (e.g., for generating radiation therapy treatment plans to be used by the radiotherapy device 110), an image acquisition device 170, a display device 180, and/or an user interface 190.

The radiotherapy device 110 may include a processor circuit 112, a memory device 116, and a communication interface 114. Memory device 116 may store computer executable instructions for an operating system 118, treatment plans 120, and any other computer executable instructions to be executed by the processor circuit 112.

Processor circuit 112 may be communicatively coupled to the memory device 116, and processor circuit 112 may be configured to execute computer executable instructions stored in the memory device 116. For example, processor circuit 112 may execute treatment plans 120 to implement functionalities of using a localization module 123, a quality module 124, a feature extraction module 127, and a classification module 126. In some embodiments, an optional supervised machine learning module 125 may also be included in memory 116 to perform training operations on the fly, for example to retrain a classifier in the clinic. In FIG. 1, supervised machine learning module 125 is depicted in dashed lines to indicate that it is an optional component. Further the processor circuit 112 may capture a plurality of images 122 from the image acquisition device 170 and store the images 122 in memory device 116. In addition, processor circuit 112 may execute the treatment plans 120 (e.g., such as Monaco® software manufactured by Elekta).

The processor circuit 112 may be a processing device, include one or more general-purpose processing devices such as a microprocessor, a central processing unit (CPU), a graphics processing unit (GPU), an accelerated processing unit (APU), or the like. More particularly, processor circuit 112 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. Processor circuit 112 may also be one or more special-purpose processing devices such as an application specific integrated circuit (ASIC), a field programmable gate array (FPGA), a digital signal processor (DSP), a System on a Chip (SoC), or the like. As would be appreciated by those skilled in the art, in some embodiments, processor circuit 112 may be a special-purpose processor, rather than a general-purpose processor. Processor circuit 112 may include one or more known processing devices, such as a microprocessor from the Pentium™, Core™, Xeon™, or Itanium® family manufactured by Intel™, the Turion™, Athlon™, Sempron™, Opteron™, FX™, Phenom™ family manufactured by AMD™, or any of various processors manufactured by Sun Microsystems. Processor circuit 112 may also include graphical processing units such as a GPU from the GeForce®, Quadro®, Tesla® family manufactured by Nvidia™, GMA, Iris™ family manufactured by Intel™, or the Radeon™ family manufactured by AMD™. Processor circuit 112 may also include accelerated processing units such as the Desktop A-4 (6, 8) Series manufactured by AMD™, the Xeon Phi™ family manufactured by Intel™. The disclosed embodiments are not limited to any type of processor(s) or processor circuits otherwise configured to meet the computing demands of identifying, analyzing, maintaining, generating, and/or providing large amounts of imaging data or manipulating such imaging data to localize and track a target or to manipulate any other type of data consistent with the disclosed embodiments. In addition, the term "processor" or processor circuit may include more than one processor, for example, a multi-core design or a plurality of processors each having a multi-core design. Processor circuit 112 can execute sequences of computer program instructions, stored in memory 116, to perform various operations, processes, methods that will be explained in greater detail below.

Memory device 116 can store image data 122 (e.g., 3D MRI, 4D MRI, 2D slices, etc.) received from the image acquisition device 170, or any other type of data/information in any format that the radiotherapy device 110 may use to perform operations consistent with the disclosed embodiments. Memory device 116 may include a read-only memory (ROM), a flash memory, a random access memory (RAM), a dynamic random access memory (DRAM) such as synchronous DRAM (SDRAM) or Rambus DRAM, a static memory (e.g., flash memory, static random access memory), etc., on which computer executable instructions are stored in any format. The computer program instructions can be accessed by the processor circuit 112, read from the ROM, or any other suitable memory location, and loaded into the RAM for execution by the processor circuit 112. For example, memory 116 may store one or more software applications. Software applications stored in memory 116 may include, for example, an operating system 118 for common computer systems as well as for software-controlled devices. Further, memory 116 may store an entire software application or only a part of a software application that is executable by processor circuit 112. For example, memory device 116 may store one or more radiation therapy treatment plans 120 generated by the treatment planning system 160. In addition, memory device 116 may store a plurality of software modules. For example, software modules can be a localization module 123, a quality module 124, a feature extraction module 127, an optional supervised machine learning module 125, and a classification module 126. The plurality of software modules may be used by the TPS 160 along with the treatment plans 120 in order to generate a radiation therapy treatment plan or update an existing radiation therapy treatment plan.

In some embodiments, memory device 116 may include a machine-readable storage medium. While the machine-readable storage medium in an embodiment may be a single medium, the term "machine-readable storage medium" should be taken to include a single medium or multiple media (e.g., a centralized or distributed database, and/or associated caches and servers) that store the one or more sets of computer executable instructions or data. The term "machine-readable storage medium" shall also be taken to include any medium that is capable of storing or encoding a set of instructions for execution by the machine and that cause the machine to perform any one or more of the methodologies of the present disclosure. The term "machine readable storage medium" shall accordingly be taken to include, but not be limited to, solid-state memories, optical and magnetic media.

In an embodiment, the memory device 116 may be configured to store at least the following types of data: DICOM data, dosage data, optimization parameters, jaw position data, beamlet data, segment data, segment shapes, voxel dose distribution data, initial dose data, and dose-volume histogram (DVH) data, image data.

The radiotherapy device 110 can communicate with a network 130 via a communication interface 114, which is communicatively coupled to processor circuit 112 and memory 116. A radiation therapy device 110 may include a source of radiation (e.g., such as a device that provides gamma rays). Communication interface 114 may include, for example, a network adaptor, a cable connector, a serial connector, a USB connector, a parallel connector, a high-speed data transmission adaptor (e.g., such as fiber, USB 3.0, thunderbolt, and the like), a wireless network adaptor (e.g., such as a WiFi adaptor), a telecommunication adaptor (e.g., 3G, 4G/LTE and the like), and the like. Communication interface 114 may include one or more digital and/or analog communication devices that permit radiotherapy device 110 to communicate with other machines and devices, such as remotely located components, via a network 130.

The network 130 may provide the functionality of a local area network (LAN), a wireless network, a cloud computing environment (e.g., software as a service, platform as a service, infrastructure as a service, etc.), a client-server, a wide area network (WAN), and the like. Therefore, network 130 can allow data transmission between the radiotherapy device 110 and a number of various other systems and devices, such as for example: the treatment planning system 160, the Oncology Information System 150, and the image acquisition device 170. Further, data generated by the treatment planning system 160, the OIS 150, and the image acquisition device 170 may be stored in the memory 116, database 140, or hospital databased 142. The data may be transmitted/received via network 130 and/or communication interface 114 in order to be accessed by the processor circuit 112.

In addition, the network 130 may be connected to the internet 132 to communicate with servers or clients that reside remotely and are connected to the internet. As described herein, network 130 may include other systems S1 (134), S2 (136), S3 (138). Systems S1, S2, and/or S3 may be identical to system 100 or may be different systems. In some embodiments, one or more systems connected to network 130 may form a distributed computing/simulation environment that collaboratively performs image acquisition, performs dose optimization, determines dose distribution, performs virtual couch shift, performs warm start optimization, conducts target location, and conducts target tracking as well as other aspects of providing radiotherapy to a patient.

Additionally, radiotherapy system 100 may communicate with the database 140 or the hospital database 142 in order to execute one or more programs stored remotely. By way of example, database 140, hospital database 142, or both may include relational databases such as Oracle™ databases, Sybase™ databases, or others and may include non-relational databases, such as Hadoop sequence files, HBase, Cassandra, or others. Such remote programs may include, for example, oncology information system (OIS) software or treatment planning software. The OIS software, for instance, may be stored on the hospital database 142, the database 140, or the OIS 150. The treatment planning software, for example, may be stored on the database 140, the hospital database 142, the treatment planning system 160 or the OIS 150. Thus, for instance, radiotherapy device 110 may communicate with the hospital database 142 to implement functionalities of the oncology information system 150.

In some embodiments, database 140 and/or hospital database 142 may be located remotely from the radiotherapy device 110. Database 140 and hospital database 142 may include computing components (e.g., database management system, database server, etc.) configured to receive and process requests for data stored in memory devices of database 140 or hospital database 142 and to provide data from database 140 or hospital database(s) 142. One skilled in the art would appreciate that databases 140, 142 may include a plurality of devices located either in a central or distributed manner.

In addition, radiotherapy device 110 may communicate with database 140 through network 130 to send/receive a plurality of various types of data stored on database 140. For example, in some embodiments, database 140 may be configured to store a plurality of images (e.g., 3D MRI, 4DMRI, 2D MRI slice images, CT images, ultrasound images, 2D Fluoroscopy images, X-ray images, raw data from MR scans or CT scans, Digital Imaging and Communications in Medicine (DICOM) data, etc.) from image acquisition device 170. Database 140 may store data to be used by the target localization module 123, the training module 124, and the treatment plans 120. The radiation therapy device 110 may receive the imaging data (e.g., 3DMRI images, 4D MRI images, ultrasound images, etc.) from the database 140.

An image acquisition device 170 can acquire medical images (e.g., Magnetic Resonance Imaging (MRI) images, 3D MRI, 2D streaming MRI, 4D volumetric MRI, Computed Tomography (CT) images, Cone-Beam CT, Positron Emission Tomography (PET) images, functional MRI images (e.g., fMRI, DCE-MRI and diffusion MRI), X-ray images, fluoroscopic image, ultrasound images, radiotherapy portal images, single-photo emission computed tomography (SPECT) images, and the like) of the patient. Image acquisition device 170 may, for example, be an MRI imaging device, a CT imaging device, a PET imaging device, an ultrasound device, a fluoroscopic device, a SPECT imaging device, or other medical imaging device for obtaining one or more medical images of the patient. Images acquired by the imaging acquisition device 170 can be stored within database 140 as either imaging data and/or test data. By way of example, the images acquired by the imaging acquisition device 170 can be also stored by the radiotherapy device 110 in memory 116.

In an embodiment, for example, the image acquisition device 170 may be integrated with the radiotherapy device 110 as a single apparatus (e.g., a MRI device combined with a linear accelerator, also referred to as a "MRI-Linac" or as an integrated MRI device combined with a Gamma Knife; a three-dimensional imager integrated with a linear accelerator; a cone-beam CT integrated with a linear accelerator, a CT-on-rails integrated with a linear accelerator; a MR-on-rails integrated with a linear accelerator). Such a MRI-Linac can be used, for example, to determine a location of a target organ or a target tumor in the patient, such as to direct radiation therapy according to the radiation therapy treatment plan to a predetermined target.

The image acquisition device 170 can be configured to acquire one or more images of the patient's anatomy for a region of interest (e.g., a target organ, a target tumor or both). The one or more images may include a plurality of 2D slices. Each 2D slice can include one or more parameters (e.g., a 2D slice thickness, an orientation, and a location, etc.). The one or more parameters can be adjusted by using the processor circuit 112, to include the target. For instance, selected features of the 2D slice can be manipulated, e.g., by adjusting the magnetic field gradient or radio frequency (RF) waveform properties. For example, the position of the slice can be varied by changing the modulation frequency of the RF pulse and maintaining the same gradient strength. Further, the orientation of the slice can be varied, for example, by using a physically different gradient axis (e.g., the selected slice can be orthogonal to the gradient applied). In an example, the image acquisition device 170 (e.g., an MRI or an MRI-Linac) can acquire a 2D slice in any orientation. For example, an orientation of the 2D slice can include a sagittal orientation, a coronal orientation, an axial orientation, or an oblique orientation. In addition, these orientations, for example, can correspond to a magnetic field gradient (e.g., Gx, Gy, or Gz, respectively) associated with the MRI or the MRI-Linac. In an example, 2D slices can be determined from information such as a 3D MRI volume. Such 2D slices can be acquired by the image acquisition device 170 in "real-time" while a patient is undergoing radiation therapy treatment, for example, when using the radiation therapy device 110. In an embodiment, the 2D image slices can be provided by an ultrasound device as an image acquisition device 170.

The treatment planning system 160 (e.g., MONACO®, manufactured by Elekta, XiO®, manufactured by Elekta) may generate and store radiation therapy treatment plans for a particular patient to be treated, radiation therapy treatment plans for other patients, as well as other radiotherapy information (e.g., beam angles, dose-histogram-volume information, the number of radiation beams to be used during therapy, the beam angles, the dose per beam, and the like). For example, treatment planning system 160 may provide information about a particular radiation dose to be applied to the patient and other radiotherapy related information (e.g., type of therapy: such as image guided radiation therapy (IGRT), intensity modulated radiation therapy (IMRT), stereotactic radiotherapy; and the like).

One type of radiation therapy treatment plan is intensity modulated radiation therapy (IMRT). IMRT differs from conformal radiation therapy, which delivers a uniform radiation field of radiation. IMRT allows the modulation of the dose distributions that are delivered by each beam. In IMRT, each beam of radiation can be discretized by dividing the aperture through which the radiation is delivered into small rectangular regions; thus, dividing each beam into a plurality of "beamlets." Using IMRT, the radiation intensities (e.g., fluence) for each beamlet can be independently modulated. For a given set of beams, the beamlet fluences can influence the quality of the treatment plan, which is determined by the ability of the radiation therapy treatment to deposit the prescribed amount of dose to cancerous targets, while simultaneous delivering a smaller amount of dose to the Organs at Risk.

Due to the unpredictable nature of the radiation beam within the patient, the dose received in a voxel may be determined, for example, through Monte Carlo simulations. A primary goal of IMRT treatment planning is to determine radiation intensities for all segments and/or apertures and/or control points and/or beamlets, which includes the MLC leaf position and intensity of all segments/apertures/control points in a beam. Although IMRT has been described above, the methods, processes, systems disclosed are not limited to IMRT, for example, they may apply to Volumetric Modulated Arc Therapy (VMAT), Intensity Modulated Arc Therapy (IMAT), dynamic MLC, helical Tomotherapy, scanned-beam therapy, and the like.

For example, VMAT delivers radiation by rotating a gantry of a radiation therapy device (see FIG. 3) through one or more arcs with the radiation beam continuously on. During a VMAT treatment, a number of parameters can be varied, such as multileaf collimator (MLC) shape, fluence output rate (e.g., dose rate), gantry rotation speed, the orientation of the MLC, and IMRT (e.g., step-and-shoot or sliding window). Typically, each arc can be divided into evenly or unevenly distributed control points, where each control point contains one beam. Each beam can be decomposed into a matrix of beamlets (e.g., where each beamlet may be $3\times10$ mm$^2$ or $3\times5$ mm$^2$, depending on the MLC size), and the radiation therapy treatment plan can be evaluated by considering the dose distribution over a discretization of the irradiated area into a number of cubes (e.g., voxels). Thus, in an embodiment, the processor circuit perform a process for updating an existing radiation therapy treatment plan using a dose distribution as a treatment objective. The existing radiation therapy treatment plan comprises a known dose distribution. In addition, the existing radiation therapy treatment plan comprises an initial set of control points, wherein the initial set of control points do not correspond to the known dose distribution. The processor can optimize the control points to approximate the known dose distribution.

Generating the treatment plan may include communicating with the image acquisition device 170 (e.g., a CT device, a MRI device, a PET device, an X-ray device, an ultrasound device, etc.) in order to access images of the patient and to delineate a target, such as a tumor. In some embodiments, the delineation of one or more organs at risk (OARS), such as healthy tissue surrounding the tumor or in close proximity to the tumor may be required. Therefore, segmentation of the OAR may be performed when the OAR is close to the target tumor. In addition, if the target tumor is close to the OAR (e.g., prostate in near proximity to the bladder and rectum), the treatment planning system 160 may allow study of the dose distribution not only in the target, but also in the OAR.

In order to delineate a target organ or a target tumor from the OAR, medical images, such as MRI images, CT images, PET images, fMRI images, X-ray images, ultrasound images, SPECT images, a set of 3D medical images and the like, of the patient undergoing radiotherapy may be obtained by the image acquisition device 170 to reveal the internal structure of a body part. Based on the information from the medical images, a 3D structure may be obtained. In addition, during a treatment planning process, many parameters may be taken into consideration to achieve a balance between efficient treatment of the target tumor (e.g., such that the target tumor receives enough radiation dose for an effective therapy) and low irradiation of the OAR(s) (e.g., the OAR(s) receives as low a radiation dose as possible), the location of the target organ and the target tumor, the location of the OAR, and the movement of the target in relation to the OAR. For example, the 3D structure may be obtained by contouring the target or contouring the OAR within each 2D layer or slice of an MRI or CT image and combining the contour of each 2D layer or slice. The contour may be generated manually (e.g., by a physician, dosimetrist, or health care worker) or automatically (e.g., using a program such as the Atlas-based Autosegmentation software, ABAS®, manufactured by Elekta, AB, Stockholm, Sweden). In certain embodiments, the 3D structure of a target tumor or an OAR may be generated automatically by the treatment planning system 160.

After the target tumor and the OAR(s) have been located and delineated, a dosimetrist, physician or healthcare worker may determine a dose of radiation to be applied to the target tumor and any OAR proximate to the tumor (e.g., left and right parotid, optic nerves, eyes, lens, inner ears, spinal cord, brain stem, and the like). After the radiation dose is determined for each anatomical structure (e.g., target tumor, OAR), a process known as inverse planning may be performed to determine one or more treatment plan parameters. The result of inverse planning may constitute a radiation therapy treatment plan that may be stored in the treatment planning system 160 or database 140. At this time, the expected degree of motion of these anatomical structures during treatment may be incorporated into the planning process. Some of these treatment parameters may be correlated. For example, tuning one parameter (e.g., weights for different objectives, such as increasing the dose to the target tumor) in an attempt to change the treatment plan may affect at least one other parameter, which in turn may result in the development of a different treatment plan. Thus, the treatment planning system 160 can generate a tailored radiation therapy treatment plan having these parameters in order for the radiotherapy device 110 to provide radiotherapy treatment to the patient.

The radiation therapy plan may be dependent on the degree of motion expected from the anatomical structures. If the structures are expected to move significantly during treatment, the quality of the treatment plan may be reduced. Also, if the structures were to move more during treatment than what was expected when the plan was made, this would reduce the effectiveness of the treatment. Therefore, localization of one or more of the anatomical structures during treatment delivery can be of benefit to the patient.

In addition, the radiotherapy system 100 includes a display device 180 and a user interface 190. The display device 180 may include one or more display screens that display medical images, interface information, treatment planning parameters (e.g., contours, dose distributions, beam angles, a set of control points, etc.) treatment plans, a target, localizing a target and/or tracking a target, or any related information to the user. The user interface 190 may be a keyboard, a keypad, a touch screen or any type of device that a user may input information to radiotherapy system 100.

Furthermore, any and all components of the radiotherapy system 100, in an embodiment, may be implemented as a virtual machine (e.g., VMWare, Hyper-V, and the like). For instance, a virtual machine can be software that functions as hardware. Therefore, a virtual machine can include at least one or more virtual processors, one or more virtual memories, and one or more virtual communication interfaces that together function as hardware. For example, the OIS 150, the TPS 160, the image acquisition device 170 could be implemented as a virtual machine. Given the processing power, memory, and computational capability available, the entire radiotherapy system could be implemented as a virtual machine.

Figure 2:
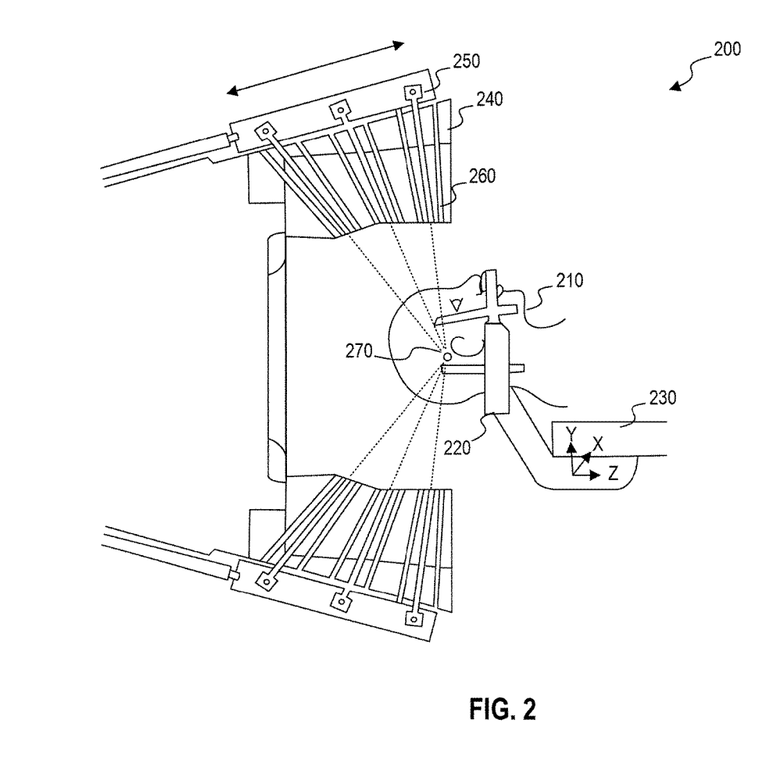
FIG. 2 illustrates an exemplary radiotherapy device, a Gamma Knife that can be used in the radiotherapy system of FIG. 1.

FIG. 2 illustrates an example of one type of radiation therapy treatment device 200, for example, a Leksell Gamma Knife, manufactured by Elekta, AB, Stockholm, Sweden. The Gamma Knife can be configured to utilize the processor device 112 (shown in FIG. 1), which may remotely access MRI images (e.g., from the image acquisition device 170) to localize a target tumor in the brain. In an embodiment, an MRI apparatus, as an image acquisition device 170, can be integrated with the Gamma Knife. As shown in FIG. 2, during a radiotherapy treatment session, a patient 210 may wear a coordinate frame 220 to keep stable the patient's body part (e.g., the head) undergoing surgery or radiotherapy. Coordinate frame 220 and a patient positioning system 230 may establish a spatial coordinate system, which may be used while imaging a patient or during radiation surgery. Radiotherapy device 200 may include a protective housing 240 to enclose a plurality of radiation sources 250. Radiation sources 250 may generate a plurality of radiation beams (e.g., beamlets) through beam channels 260. The plurality of radiation beams may be configured to focus on an isocenter 270 from different directions. While each individual radiation beam may have a relatively low intensity, isocenter 270 may receive a relatively high level of radiation when multiple doses from different radiation beams accumulate at isocenter 270. In certain embodiments, isocenter 270 may correspond to a target under surgery or treatment, such as a tumor.

Figure 3:
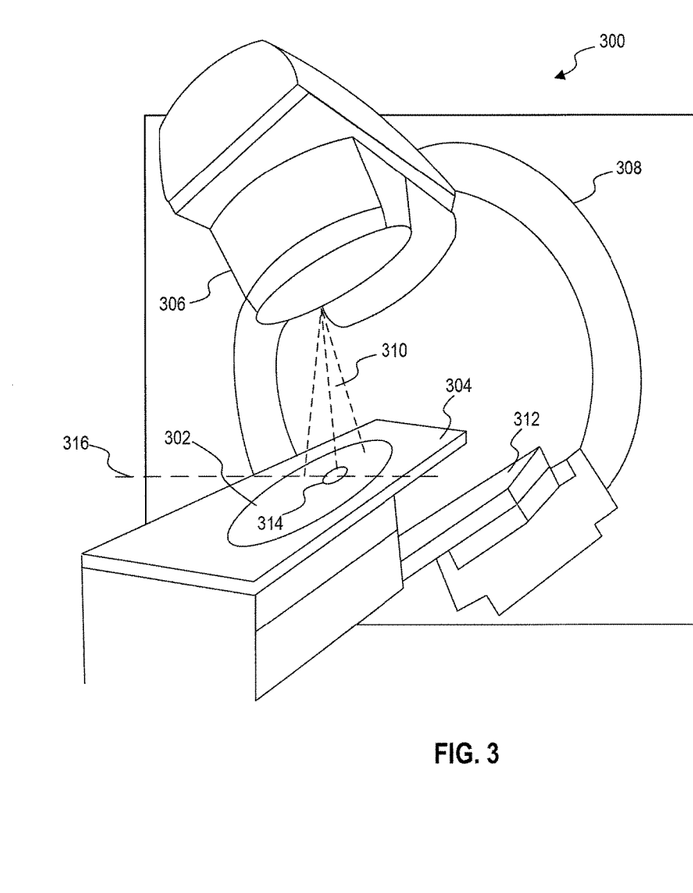
FIG. 3 illustrates an exemplary radiotherapy device, a linear accelerator that can be used in the radiotherapy system of FIG. 1.

FIG. 3 illustrates another example of a type of radiation therapy device 300 (e.g., a linear accelerator, referred to as a LINAC, manufactured by Elekta, AB, Stockholm, Sweden). When using the linear accelerator 300, a patient 302 may be positioned on a patient table 304 to receive the radiation dose determined by a radiation therapy treatment plan generated by the treatment planning system 160 (shown in FIG. 1). The image data 122 and localization module 123 can be used to localize and track a 3D target in a volume, such as a target organ or a target tumor located within the anatomy of the patient 302.

The linear accelerator 300 may include a radiation head 306 connected to a gantry 308 that rotates around the patient 302. The radiation head 306 generates a radiation beam 310 that is directed toward the target organ or target tumor. As the gantry 308 rotates, the radiation head 306 can rotate around the patient 302. While rotating, the radiation head 306 may provide patient 302 with a plurality of varying dosages of radiation depending upon the angle and the shape and size of the tumor according to the treatment plan generated by the treatment planning system 160 (shown in FIG. 1). Because organs and tumors move within a patient's body, fast and accurate 3D localization of the target is important. For instance, a target organ or tumor may move because of various types of motion (e.g., respiratory, cardiac, peristalsis or other types of patient motion). Therefore, the linear accelerator 300 may be configured to localize the target (e.g., organ or tumor) and track the target during radiation therapy treatment by using target localization module 123.

In addition, below the patient table 304, a flat panel scintillator detector 312 may be provided, which may rotate synchronously with the radiation head 306 around an isocenter 314 located on a target organ or a target tumor on the body of the patient 32. The flat panel scintillator can acquire images with the highest achievable signal-to-noise ratio and can be used for verification of the amount of radiation received by the patient 302 during any particular radiation therapy treatment session (e.g., a radiation therapy treatment may require multiple sessions of radiation therapy, where each session is typically referred to as a 'fraction'). Further, such images are used to determine the geometric accuracy of patient positioning relative to the radiation head 306.

The intersection of an axis 316 with the center of the beam 310, produced by the radiation head 306, is usually referred to as the "isocenter". The patient table 304 may be motorized so the patient 302 can be positioned with the tumor site at or close to the isocenter 314. For instance, the patient table 304 may change positions relative to one or more other components of the linear accelerator 300, such as to elevate, change the longitudinal position, or the latitudinal position of the patient 302 relative to a therapeutic radiation source located in the radiation head 306.

Figure 4:
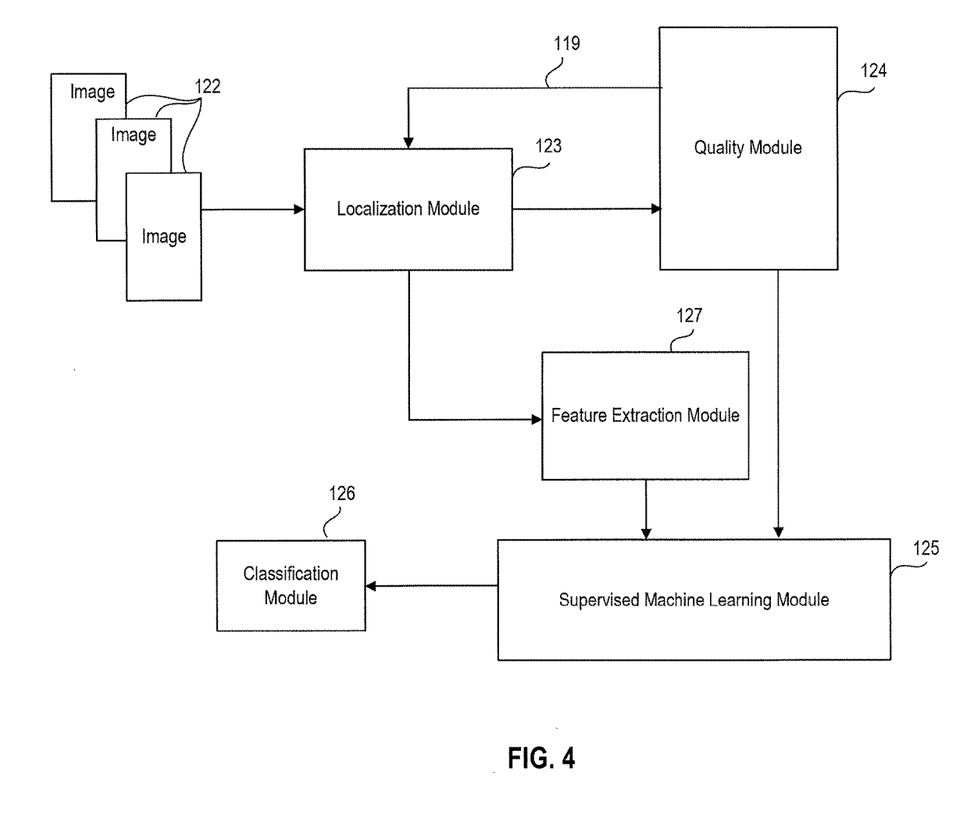
FIG. 4 depicts a block diagram illustrating training a classifier.

As described above, there is a need for a method and system that can quickly, efficiently, and automatically determine in real-time the quality of the localization of a target in an image, which can provide information as to a change in patient positioning and target motion during radiation therapy treatment. This method and system may continuously validate that the detected changes are known with confidence. FIG. 4 depicts a block diagram illustrating generating and training a classifier using supervised machine learning as one embodiment. A plurality of medical images 122 (e.g., CT, MRI, ultrasound and the like) are stored in memory 116. The images 122, for example, can be three-dimensional volumes representing a time series of observations of a prostate. In another embodiment, the images 122 can be two-dimensional images. The images 122 may include images taken prior to radiation therapy treatment and/or during radiation therapy treatment. The training data may be obtained under conditions which do not involve real treatment, but are only representative of it. As the target moves, additional images 122 may be taken and stored in memory 116.

After the images 122 are captured and stored, the images 122 can be retrieved from memory 116 by processor 112, and the processor can retrieve a localization module 123 where image registration is performed. In an embodiment, the localization of the anatomy may be performed by the localization module 123 that uses, for example, a rigid six parameter transformation (e.g., 3 rotations and 3 translations). The localization module 123 can, for example, register the current volumetric dataset to the first volumetric dataset taken. In another embodiment, the localization module can use segmentation to identify the target in each image. In another embodiment, the localization module can use a spatial hashing technique to identify the location from the appearance of the target alone. The localization process provides a mapping between at least two images to provide an indication if the target has moved.

The localization process by itself does not define a measure of quality. It may be necessary to define what is meant by quality in a specific application. For example, "good quality" may be defined as better than about 0.5 mm of precision, "poor quality" may be defined as precision between about 0.5 mm and about 2 mm, and a failure in localization may be defined as greater than about 2 mm in precision. The image sets provided for initial training may be selected to provide "good quality" results.

In order to collect a plurality of localization results of all the different types of qualities, the precision of the localization process can be changed. Thus, the quality module 124 is connected to the localization module 123 via a feedback loop 119. For example, in an embodiment, the localization process may use a registration algorithm. The registration algorithm may use an initial guess of what is the "correct" localization result to start the algorithm. The values of the "initial guess" can be changed. For example, the "initial guess" can be continuously adjusted from an ideal value. By changing the initial starting point of the localization process a plurality of localization results may be obtained and stored in memory 116. In this way, abnormal conditions can be created for the localization algorithm by moving the initial guess further from ideal. Adjustment of the initial guess can continue until poor quality or failure results occur. By creating an abnormal condition to cause the localization algorithm to fail, a plurality of poor quality and failed cases can be generated to train the machine learning module 125. The results of the localization module 123 are input to both the quality module 124 and the feature extraction module 127.

The feature extraction module 127 extracts a plurality of features from the localized images. In an embodiment, the features may include a correlation score, a Kullback Leiber distance between histograms, a minimum correlation score and a maximum correlation score of the tracked object divided into octants, correlation scores 1 mm away from a found position, an inverse compositional Hessian scale factor, and combinations thereof.

Once a measure of quality is determined by the quality module 124 for each of the localized images, and the features have been extracted by the feature extraction module 127, a supervised machine learning module 125 can be used to train a classifier. Various types of machine learning can be implemented by the supervised machine learning module 125, such as Fisher discriminant analysis, Kernel density estimators, random forests, support vector machines, and the like. The supervised machine learning module 125 uses machine learning to create a plurality of subsets of features, determine which of the subsets of features is the best subset of features (primary features), and uses this best subset of features to train a classifier. For instance, the features used may include one or more of a correlation score, a similarity measure (e.g., a correlation score) computed a predetermined distance away from the found localization, similarity scores on subsets of the localized target, an inverse compositional Hessian scale factor, the Kullback-Leibler distance between histograms, internal subtotals or other subcomputations of the similarity measure. In an embodiment, the list of primary features can be used to train the classifier. In one embodiment, the list of primary features may include at least four features (e.g., correlation score, 1 mm window away, minimum and maximum orthant score) that can be used to train the classifier.

The output of the supervised machine learning module 125 is a classification module 126 (e.g., a trained classifier) that is stored in memory 116. The classification module 126 can be used to predict the quality of the image localization for future image localizations. By predicting the quality of the image localizations, the classification module 126 can provide an estimate of the quality of the tracking of a target. For example, whether the tracking is within a certain precision or whether the tracking has been lost.

Figure 5:
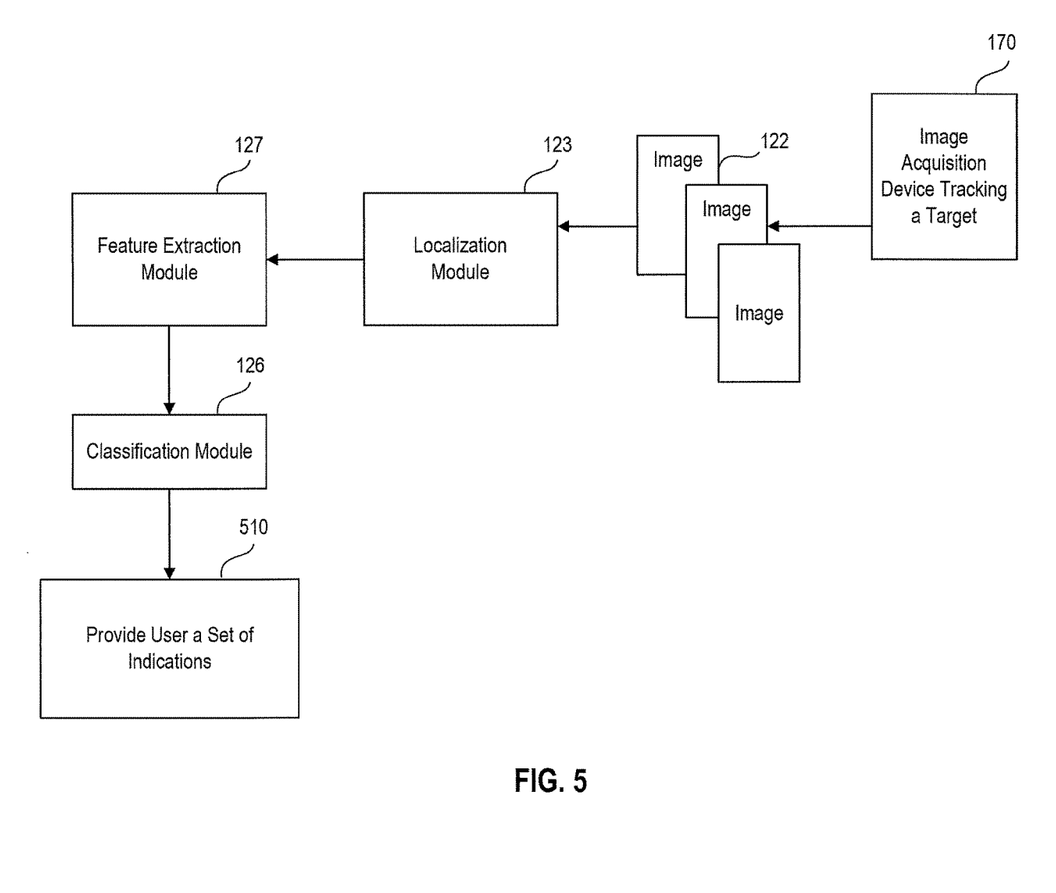
FIG. 5 depicts a block diagram illustrating using the classifier of FIG. 4 for target tracking.

FIG. 5 depicts a block diagram illustrating using the classifier of FIG. 4 for target tracking. In an embodiment, an image acquisition device 170 (e.g., shown in FIG. 1) can be used to acquire a plurality of images 122. For example, an image acquisition device 170 can be an ultrasound device. As the image acquisition device 170 acquires images 122 as it tracks a moving target in real-time, for each tracking step (e.g., about 0.5 mm) image slices of the target volume are acquired by the image acquisition device 170. A four-dimensional (4D) monitoring algorithm (not shown) acquires the image slices and cumulates the data, constantly repeating in real-time until an image 122 is ready for localization. In an embodiment the image 122 may be a single image. In another embodiment, the image 122 may be a plurality of images. The processor 112 retrieves the localization module 123 from memory 116 and applies the images 122 to the localization module 123. The localization module 123 determines a localization result for each image 122. After the images 122 are localized, the processor 112 retrieves the feature extraction module 127 and the classification module 126 from memory 116. The feature extraction module 127 extracts the necessary features from the images and the localization result, and the classification module 126 uses the previously learned classifier to provide a user an indication of target tracking quality. For example, the classification module 126 indicates whether the localization result has normal confidence, low confidence, or if tracking has been lost. The output of the classification module 126 provides the user an indication (510) of whether to leave the radiation beam turned on and continue radiation therapy, or whether to turn the radiation beam off because target tracking has been lost. In another embodiment, the radiation beam can be automatically turned off when the classification module 126 indicates that the target has lost tracking.

An advantage of using a classifier is that the classifier, in an embodiment, can be updated or retrained, as it is used in a clinical environment. For instance, as additional data is acquired from the clinical environment, the classifier can be retrained on the fly based on the additional data. The updated or retrained classifier may improve the prediction results.

Figure 6:
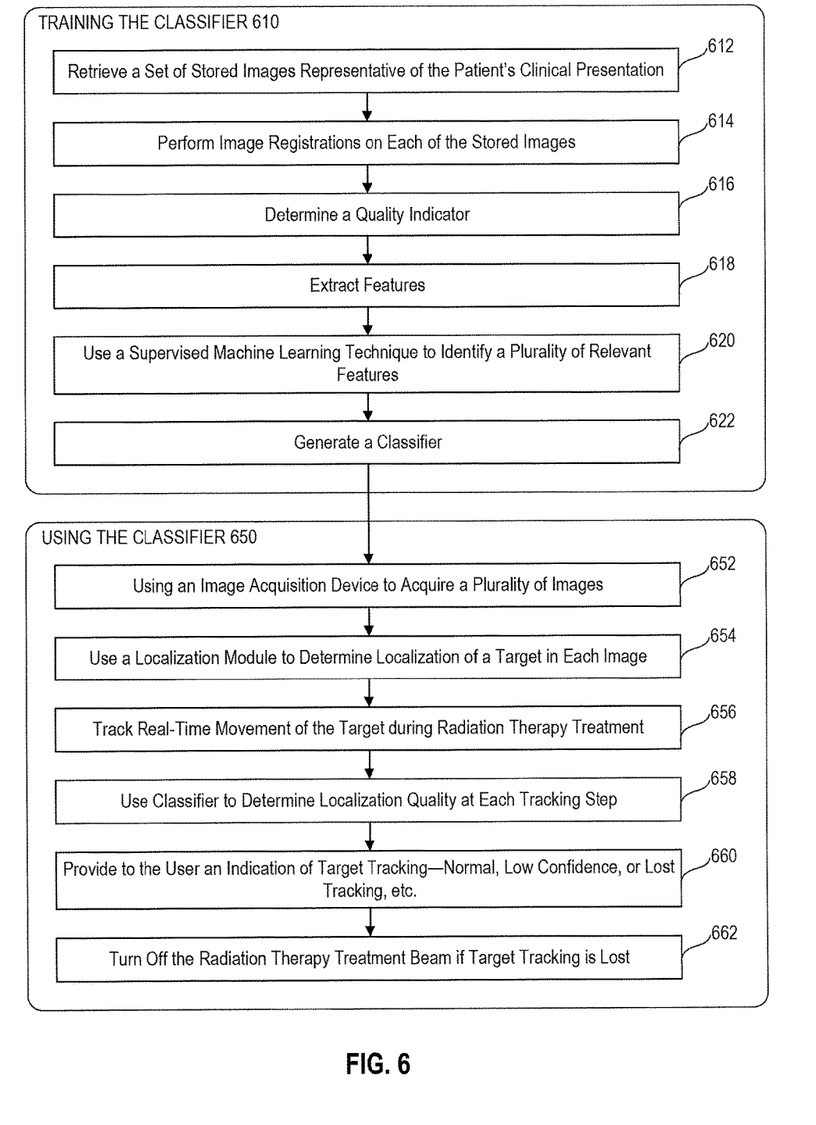
FIG. 6 illustrates a flow chart of an exemplary method to track a moving target during radiation therapy using the classifier of FIG. 4.

FIG. 6 illustrates a flow chart of an exemplary method to train a classifier and to track a moving target during radiation therapy using the trained classifier. The flow chart shown in FIG. 6 includes two parts. The first part is for training the classifier, which can be performed during product development phase or any pre-treatment configuration or calibration. As discussed above, the classifier can be retrained based on additional data when it is used in clinical environment. The second part is for using the classifier to evaluate localization quality, which can be performed during treatment. Based on the localization quality, an indication can be provided to a user to inform the user the localization quality. Alternatively or additionally, the radiation beam can be automatically gated based on the localization quality.

As shown in FIG. 6, the first part 610 includes steps for training the classifier. Training the classifier can be performed in any stage before using the classifier and the training process is not necessarily performed by processor 112 of radiotherapy device 110. In some embodiments, a classifier may be retrained in clinic environment based on updated image data, and the retraining process may be performed by processor 112. In the following description, reference will be made to processor 112, as an example, when describing steps in the training process. However, it should be understood that the training process can also be performed by any other processors.

In steps 612, processor device 112 may retrieve a set of stored images 122 representative of the patient's clinical presentation (e.g., ultrasound images, MR images, etc.). In step 614, processor 112 may execute functions provided by localization module 123 to perform image registrations on each of the stored images. In step 616, processor 112 may determine a quality indicator based on the image registration results and quality measure provided by quality module 124. In step 618, processor 112 may execute functions provided by feature extraction module 127 to extract features from the images from which the quality indicator is determined. In step 620, processor 112 may use a supervised machine learning technique provided by supervised machine learning module 125 to identify a plurality of relevant features. In step 622, processor 112 may generate a classifier using classification module 126.

The second part 650 includes steps for using the classifier during treatment to determine localization quality. In step 652, a plurality of images may be acquired by image acquisition device 170. In step 654, processor 112 may use localization module 123 to determine localization of a target (e.g., a tumor, an organ, an OAR, etc.) in each image. In step 656, processor 112 may track real-time movement of the target during radiation therapy treatment. In step 658, processor 112 may use the classifier trained in part 1 (610) to determine localization quality at each tracking step. In step 660, processor 112 may provide an indication to the user of radiotherapy device 110, which may indicate the quality of target tracking. The quality may include quality measures such as normal, low confidence, lost tracking, etc. In step 662, processor 112 may control the radiation dose application based on the quality, such as gating the radiation beam when the tracking quality is not normal, turning off the radiation therapy treatment beam if target tracking is lost, etc.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

The exemplary disclosed embodiments describe systems and methods for target tracking using a quality indicator during radiation therapy. The foregoing description has been presented for purposes of illustration. It is not exhaustive and is not limited to the precise forms or embodiments disclosed. Modifications and adaptations of the embodiments will be apparent from consideration of the specification and practice of the disclosed embodiments.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, an apparatus, system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include software code, such as microcode, assembly language code, a higher-level language code, or the like. The various programs or program modules can be created using a variety of software programming techniques. For example, program sections or program modules can be designed in or by means of Java, Python, C, C++, assembly language, or any known programming languages. One or more of such software sections or modules can be integrated into a computer system and/or computer-readable media. Such software code can include computer readable instructions for performing various methods. The software code may form portions of computer program products or computer program modules. Further, in an example, the software code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

Moreover, while illustrative embodiments have been described herein, the scope includes any and all embodiments having equivalent elements, modifications, omissions, combinations (e.g., of aspects across various embodiments), adaptations or alterations based on the present disclosure. The elements in the claims are to be interpreted broadly based on the language employed in the claims and not limited to examples described in the present specification or during the prosecution of the application, which examples are to be construed as non-exclusive. Further, the steps of the disclosed methods can be modified in any manner, including by reordering steps or inserting or deleting steps. It is intended, therefore, that the specification and examples be considered as example only, with a true scope and spirit being indicated by the following claims and their full scope of equivalents.

The above description is intended to be illustrative, and not restrictive. For example, the above-described examples (or one or more aspects thereof) may be used in combination with each other. Other embodiments can be used, such as by one of ordinary skill in the art upon reviewing the above description. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A method for training a classifier for determining a quality of target localization from a plurality of images acquired by an imaging device during radiation therapy treatment to a patient, the method comprising:
   determining a localization result indicating a location of a target in a plurality of images representative of images acquired in a radiation therapy treatment session;
   determining a quality indicator for each localization result, the quality indicator representing a precision level of each localization result;
   extracting, by processing circuitry, one or more features from each localization result; and
   training the classifier using the localization result, the quality indicator, and one or more of the extracted features, the classifier outputs an indication of the precision level of a new localization result of a newly captured image.

2. The method of claim 1, further comprising:
   selecting a subset of images from the plurality of images to provide a quality measure; and
   providing samples having a plurality types of qualities by adjusting the localization result.

3. The method of claim 1, wherein training the classifier comprises:
   training the classifier using a supervised machine learning technique, including:
   creating a plurality of subsets of features;
   determining primary features based on the plurality of subsets of features; and
   training the classifier using the primary features.

4. The method of claim 3, wherein the primary features include at least one of:
   a correlation score;
   a similarity measure computed a predetermined distance away from the location of the target;
   a minimum orthant score; or
   a maximum orthant score.

5. The method of claim 1, wherein the imaging device includes an ultrasound probe and the plurality of images include ultrasound images.

6. The method of claim 1, wherein the imaging device includes an MRI device and the plurality of images include MR images.

7. A method for determining a quality of target localization from a plurality of images acquired by an imaging device during radiation therapy treatment to a patient, the method comprising:
   determining a localization result indicating a location of a target in a plurality of images acquired during radiation therapy treatment to the patient;
   determining a localization quality of the localization result for tracking the location of the target using a classifier, the localization quality representing a precision level of each localization result; and
   providing to a user an indication of the localization quality or taking treatment related action based on the localization quality.

8. The method of claim 7, wherein the indication of the localization quality reflects a determination of at least a normal tracking, a low confidence tracking, and a lost tracking.

9. The method of claim 7, further comprising:
   extracting, using processing circuitry, one or more features from the plurality of images and the location result; and
   determining the localization quality using the classifier based on the extracted one or more features.

10. The method of claim 7, further comprising:
    tracking real-time movement of the target during the radiation therapy treatment based on the localization result and the localization quality.

11. The method of claim 7, wherein the treatment related action includes turning off a radiation beam when the localization quality indicates a lost tracking of the target.

12. The method of claim 7, further comprising:
    updating or retraining the classifier in a clinical environment based on new data.

13. A system for training a classifier for determining a quality of target localization from a plurality of images acquired by an imaging device during radiation therapy treatment to a patient, the system comprising:
   a memory for storing computer-executable instructions; and
   a processor communicatively coupled to the memory, wherein the computer-executable instructions, when executed by the processor, cause the processor to perform operations including:

determining a localization result indicating a location of a target in a plurality of images representative of images acquired in a radiation therapy treatment session;

determining a quality indicator for each localization result, the quality indicator representing a precision level of each localization result;

extracting one or more features from each localization result; and training the classifier using the localization result, the quality indicator, and one or more of the extracted features, the classifier outputs an indication of the precision level of a new localization result of a newly captured image.

14. A system for determining a quality of target localization from a plurality of images acquired by an imaging device during radiation therapy treatment to a patient, the system comprising:

a memory for storing computer-executable instructions; and a processor communicatively coupled to the memory, wherein the computer-executable instructions, when executed by the processor, cause the processor to perform operations including:

determining a localization result indicating a location of a target in a plurality of images acquired during radiation therapy treatment to the patient;

determining a localization quality of the localization result for tracking the location of the target using a classifier, the localization quality representing a precision level of each localization result; and providing to a user an indication of the localization quality or taking treatment related action based on the localization quality.

15. The system of claim 14, wherein the indication of the localization quality reflects a determination of at least a normal tracking, a low confidence tracking, and a lost tracking.

16. The system of claim 14, wherein the operations further comprise:

extracting one or more features from the plurality of images and the location result; and determining the localization quality using the classifier based on the extracted one or more features.

17. A non-transitory computer-readable medium that stores a set of instructions that is executable by at least one processor of a device to cause the device to perform a method for training a classifier for determining a quality of target localization from a plurality of images acquired by an imaging device during radiation therapy treatment to a patient, the method comprising:

determining a localization result indicating a location of a target in a plurality of images representative of images acquired in a radiation therapy treatment session;

determining a quality indicator for each localization result, the quality indicator representing a precision level of each localization result;

extracting, by the at least one processor, one or more features from each localization result; and training the classifier using the localization result, the quality indicator, and one or more of the extracted features, the classifier outputs an indication of the precision level of a new localization result of a newly captured image.

18. A non-transitory computer-readable medium that stores a set of instructions that is executable by at least one processor of a device to cause the device to perform a method for determining a quality of target localization from a plurality of images acquired by an imaging device during radiation therapy treatment to a patient, the method comprising:

determining a localization result indicating a location of a target in a plurality of images acquired during radiation therapy treatment to the patient;

determining a localization quality of the localization result for tracking the location of the target using a classifier, the localization quality representing a precision level of each localization result; and providing to a user an indication of the localization quality or taking treatment related action based on the localization quality.

19. The non-transitory computer-readable medium of claim 18, wherein the indication of the localization quality reflects a determination of at least a normal tracking, a low confidence tracking, and a lost tracking.

20. The non-transitory computer-readable medium of claim 18, wherein the method further comprises:

extracting, by the at least one processor, one or more features from the plurality of images and the location result; and determining the localization quality using the classifier based on the extracted one or more features.

* * * * *